US00PP26919P2

(12) United States Plant Patent
Zaiger et al.

(10) Patent No.: US PP26,919 P2
(45) Date of Patent: Jul. 12, 2016

(54) PEACH TREE NAMED 'JUNE HONEY'

(50) Latin Name: *Prunus persica*
Varietal Denomination: June Honey

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 20 days.

(21) Appl. No.: 14/544,663

(22) Filed: Feb. 2, 2015

(51) Int. Cl.
*A01H 5/08* (2006.01)

(52) U.S. Cl.
USPC ..... Plt./197

(58) Field of Classification Search
USPC ..... Plt./197
CPC ..... A01H 5/0868
See application file for complete search history.

*Primary Examiner* — Kent L Bell

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size fruit.
3. Fruit with a mild, sweet, sub-acid flavor and very good eating quality.
4. Fruit with good storage and shipping quality.
5. Fruit with attractive red skin color.

1 Drawing Sheet

Botanical designation: *Prunus persica.*
Variety denomination: 'June Honey'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricot, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Sierra Rich' Peach (U.S. Plant Pat. No. 12,391) and our proprietary non-patented peach seedlings '209LP573', '57ZA266', '215LC14', '374LH329', '216LK450', '58EG517' and '170LE418'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between our proprietary non-patented peach seedlings '209LP573' and '216LK450'. The seed parent (209LP573) originated as an open pollinated seedling from our proprietary non-patented peach seedling '57ZA266'. '57ZA266' is a first generation seedling from the cross of our proprietary non-patented peach seedling '215LC14' and '374LH329'. The pollen parent (216LK450) was developed from the cross of our proprietary peach seedlings '58EG517' and '170LE418'. A large number of these first generation seedlings were grown and budded to older trees of 'Nemaguard' Rootstock (non-patented) to accelerate rapid fruit production. Under close and careful observation we recognized the desirable tree and fruit characteristics of the present seedling and selected it in 2007 for additional asexual propagation and commercialization.

ASEXUAL REPRODUCTION OF THE VARIETY

In 2007 asexual reproduction of the new and distinct variety of peach tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a productive and regular bearer of large size, yellow flesh, freestone fruit with mild, sweet, sub-acid flavor and very good eating quality. The fruit is further characterized by having good handling and storage ability. In comparison to its seed parent (209LP573)

the tree of the new variety has a more consistent and heavier fruit production and the fruit is approximately 5 days earlier in maturity. In comparison to its pollen parent (216LK450) the fruit of the new variety has firmer flesh and is approximately 12 days earlier in maturity. In comparison to the commercial variety 'Sierra Rich' Peach (U.S. Plant Pat. No. 12,391) the tree of the new variety requires approximately 250 hours less winter chilling and the fruit is approximately 9 days earlier in maturity and larger in size.

DESCRIPTION OF THE PHOTOGRAPH

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size. Fruit set varies with climatic conditions during bloom time.

*Bearer*.—Regular, adequate fruit set 5 consecutive years. No alternate bearing observed.

*Fertility*.—Self fertile.

*Density*.—Medium dense, pruning to vase shape desirable for sunlight penetration to center of tree to enhance fruit color and health of fruit wood.

*Hardiness*.—Hardy in all stone fruit growing areas of California. Tree grown in USDA Hardiness Zone 9. Winter chilling requirement approximately 600 hours at or below 45° F.

Trunk:

*Size*.—Large, average circumference 50.8 cm at 27.9 cm above ground on a 7 year old tree.

*Stocky*.—Medium stocky.

*Texture*.—Medium shaggy, roughness increases with age.

*Color*.—Varies from 10YR 8/2 to 2.5Y 7/2.

Branches:

*Size*.—Medium to large. Average circumference 20.3 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 20 in a 25.8 square cm section. Average length 4.4 mm. Average width 2.2 mm. Color varies from 7.5YR 7/10 to 10YR 6/12.

*Color*.—New growth varies from 5GY 6/6 to 5GY 6/8. Mature growth varies from 7.5YR 6/2 to 10YR 3/4, varies with age of growth.

Leaves:

*Size*.—Large. Average length 148.1 mm. Average width 41.7 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 9.6 mm. Average width 1.8 mm. Longitudinally grooved. Surface — glabrous. Color varies from 5GY 5/6 to 5GY 4/6.

*Glands*.—Type — reniform. Size — large. Average length 1.5 mm. Average diameter 1.2 mm. Number varies from 3 to 7, average number 4. Located primarily on the base of the leaf blade and the upper portion of the petiole. Color varies from 10Y 7/8 to 2.5GY 7/8.

*Stipules*.—Average number — 2. Average length 10.1 mm. Edges — pectinate. Color varies from 2.5GY 6/8 to 2.5GY 6/10.

*Color*.—Upper surface varies from 2.5GY 3/4 to 5GY 3/4. Lower surface varies from 5GY 5/4 to 5GY 4/4. Midvein color varies from 10Y 8/4 to 2.5GY 8/4.

Flower buds:

*Size*.—Large. Average length 19.7 mm. Average diameter 10.9 mm.

*Hardiness*.—Hardy in all stone fruit growing areas of California.

*Density*.—Medium dense.

*Form*.—Conical, becoming elongated just before opening.

*Pedicel*.—Average length 5.3 mm. Average width 1.2 mm. Color varies from 5GY 6/6 to 5GY 5/6. Surface glabrous.

*Color*.—Varies from 7.5RP 6/12 to 5RP 8/6.

Flowers:

*Blooming period*.—Date of First Bloom Feb. 11, 2014. Date of Petal Fall Feb. 21, 2014, varies slightly with climatic conditions.

*Size*.—Large, showy. Average height 23.1 mm. Average diameter 41.7 mm.

*Petals*.—Normally 5, alternately arranged to sepals. Size — large. Average length 20.1 mm. Average width 19.7 mm. Form — orbicular. Apex rounded. Base — rounded to somewhat truncate. Margin — sinuate. Both upper and lower surfaces glabrous. Color varies from 5RP 8/4 to 5RP 8/6.

*Sepals*.—Normally 5, alternately arranged to petals. Size — large. Average length 5.9 mm. Average width 6.6 mm. Shape — ovate, apex rounded. Margin — entire. Color — upper surface varies from 5GY 5/6 to 5R 3/4. Lower surface varies from 5R 2/4 to 7.5R 2/2. Upper surface glabrous, lower surface pubescent.

*Stamens*.—Average number per flower 54. Average filament length 16.7 mm. On average, the stamens are even with the height of the petals. Filament color varies from N 9.5/ (white) to 5RP 7/10 depending on age of flower. Anther color varies from 7.5R 4/12 to 5Y 8/10.

*Pollen*.—Self fertile. Color varies from 2.5Y 7/12 to 5Y 7/12.

*Pistil*.—Number — normally one. Surface — pubescent. Average length 16.4 mm. Position of stigma an average of 2.5 mm below anthers. Color varies from 10Y 8/4 to 2.5GY 8/4.

*Fragrance*.—Slight.

*Color*.—Varies from 5RP 8/4 to 5RP 8/6.

*Pedicel*.—Average length 4.8 mm. Average width 1.3 mm. Color varies from 5GY 6/6 to 5GY 5/6. Surface — glabrous.

*Number flowers per flower bud*.—Normally one.

Fruit:

*Maturity when described*.—Firm ripe and ready for consumption.

*Date of first picking*.—Jun. 15, 2014.

*Date of last picking*.—Jun. 25, 2014, varies slightly with climatic conditions.

*Size*.—Large. Average diameter axially 66.4 mm. Average transversely in suture plane 75.5 mm. Average weight 210.2 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Retuse.

*Base*.—Retuse.

*Stem cavity*.—Rounded to slightly elongated in suture plane. Average depth 9.1 mm. Average diameter 8.7 mm.

Stem:

*Size*.—Medium. Average length 9.2 mm. Average diameter 3.9 mm.

*Color*.—Varies from 2.5GY 6/8 to 5GY 6/8.

Flesh:

*Ripens*.—Evenly.

*Texture*.—Firm, meaty and crisp.

*Fibers*.—Few, small, tender.

*Firmness*.—Good, comparable to other commercial varieties.

*Aroma*.—Moderate.

*Amydgalin*.—Undetected.

*Eating quality*.—Very good.

*Flavor*.—Very good, a mild, sweet, sub-acid flavor.

*Juice*.—Heavy amount, enhances flavor.

*Acidity*.—Not available.

*Brix*.—Average Brix 19.0°, varies slightly with amount of fruit per tree and climatic conditions.

*Pit cavity*.—Average length 36.4 mm. Average width 26.7 mm. Average depth 11.3 mm. Color varies from 2.5Y 8/8 to 7.5R 4/10 next to stone.

*Color*.—Varies from 10YR 8/8 to 2.5Y 8/10.

Skin:

*Thickness*.—Medium.

*Surface*.—Smooth.

*Pubescence*.—Pubescent, very short.

*Tendency to crack*.—None.

*Color*.—Ground color varies from 10YR 8/8 to 2.5Y 8/6. Overspread with 5R 3/8 to 7.5R 4/10.

*Tenacity*.—Tenacious to flesh.

*Astringency*.—None.

Stone:

*Type*.—Clingstone, weak adherence to flesh.

*Size*.—Large. Average length 35.4 mm. Average width 25.7 mm. Average thickness 20.5 mm.

*Form*.—Obovoid.

*Base*.—Flat.

*Apex*.—Pointed. Average length 2.7 mm.

*Surface*.—Pitted throughout, pits vary from rounded to elongated.

*Sides*.—Unequal, one side extending further from suture plane.

*Ridges*.—Relatively smooth, extending from base to apex.

*Tendency to split*.—None.

*Color*.—Varies from 7.5YR 7/6 to 7.5YR 6/6 when dry.

Kernel:

*Size*.—Medium to large. Average length 17.8 mm. Average width 9.7 mm. Average depth 7.1 mm.

*Form*.—Ovoid.

*Viability*.—Viable, complete embryo development.

*Skin color*.—Varies from 5Y 9/4 to 5Y 9/6.

Use: Dessert.

*Market*.—Local and long distance.

Keeping quality: Good, held firm in cold storage for 3 weeks at 38° to 42° F. without internal breakdown or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

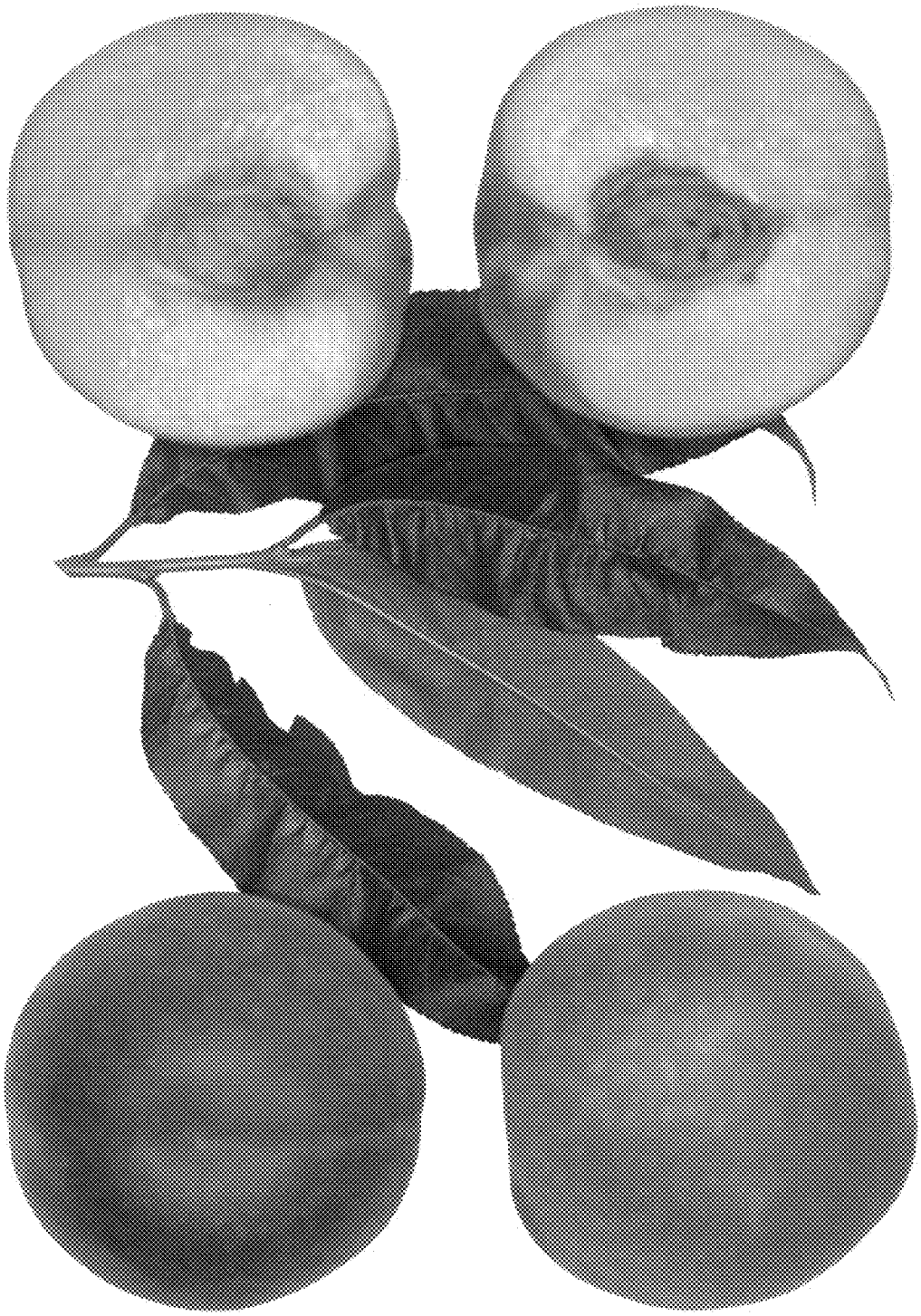

* * * * *